United States Patent
Grum-Schwensen et al.

(10) Patent No.: US 9,629,779 B2
(45) Date of Patent: Apr. 25, 2017

(54) OSTOMY SEALING MEMBER PACKAGE AND AN OSTOMY SEALING MEMBER THEREFORE

(75) Inventors: Christen Grum-Schwensen, Hillerød (DK); Vigdis Hannestad, Bergen (NO)

(73) Assignee: Hollister Incorporated, Libertyville, IL (US)

( * ) Notice: Subject to any disclaimer, the term of this patent is extended or adjusted under 35 U.S.C. 154(b) by 25 days.

(21) Appl. No.: 14/233,059

(22) PCT Filed: Jul. 26, 2012

(86) PCT No.: PCT/EP2012/064692
§ 371 (c)(1),
(2), (4) Date: Feb. 24, 2014

(87) PCT Pub. No.: WO2013/014231
PCT Pub. Date: Jan. 31, 2013

(65) Prior Publication Data
US 2014/0163496 A1 Jun. 12, 2014

(30) Foreign Application Priority Data
Jul. 28, 2011 (EP) .................................. 11175758

(51) Int. Cl.
*A61F 5/443* (2006.01)
*A61J 1/00* (2006.01)
*A61F 5/445* (2006.01)

(52) U.S. Cl.
CPC ................ *A61J 1/00* (2013.01); *A61F 5/443* (2013.01); *A61F 5/445* (2013.01)

(58) Field of Classification Search
USPC ......................................................... 604/338
See application file for complete search history.

(56) References Cited

U.S. PATENT DOCUMENTS

| | | | | |
|---|---|---|---|---|
| 3,081,771 A | * | 3/1963 | Lee | A61F 5/443 604/344 |
| 3,558,406 A | * | 1/1971 | Kugler | B31B 23/00 156/251 |
| 3,690,320 A | * | 9/1972 | Riely | A61F 5/441 604/333 |

(Continued)

FOREIGN PATENT DOCUMENTS

| | | |
|---|---|---|
| EP | 0652155 A1 | 5/1995 |
| GB | 2152387 A | 8/1985 |

(Continued)

OTHER PUBLICATIONS

International Search Report and Written Opinion of the International Searching Authority (European Patent Office) issued Nov. 5, 2012.

*Primary Examiner* — Tatyana Zalukaeva
*Assistant Examiner* — Guy K Townsend
(74) *Attorney, Agent, or Firm* — Levenfeld Pearlstein, LLC (57) ABSTRACT

The present disclosure concerns a package for an ostomy sealing member for sealing around a stoma in relation to an ostomy appliance, said sealing member comprising a hypoallergenic, moldable adhesive material, said sealing member having an annular periphery and an opening therein for receiving a stoma, wherein the opening is non-concentric with the periphery.

15 Claims, 9 Drawing Sheets

(56) References Cited

U.S. PATENT DOCUMENTS

| | | | | |
|---|---|---|---|---|
| 3,734,096 A * | 5/1973 | Millenbach | A61F 5/441 | 604/355 |
| 3,787,290 A * | 1/1974 | Kaye | C12M 23/12 | 435/288.4 |
| 4,445,898 A * | 5/1984 | Jensen | | 604/337 |
| 4,701,169 A * | 10/1987 | Steer | A61F 5/443 | 604/338 |
| 4,854,475 A * | 8/1989 | Riihimaki | A61L 2/26 | 206/369 |
| 4,930,942 A * | 6/1990 | Keyes | A61F 5/445 | 406/49 |
| 4,983,172 A * | 1/1991 | Steer | A61F 5/4405 | 24/30.5 P |
| 5,051,259 A | 9/1991 | Olsen et al. | | |
| 5,135,519 A * | 8/1992 | Helmer | A61F 5/445 | 604/332 |
| 5,306,504 A * | 4/1994 | Lorenz | A61F 13/023 | 424/401 |
| 5,545,154 A * | 8/1996 | Oberholtzer | A61F 5/443 | 604/336 |
| 5,603,203 A * | 2/1997 | Robache | | 53/559 |
| 5,755,514 A * | 5/1998 | Baar-Bartelt | B65D 31/10 | 383/104 |
| 5,846,620 A * | 12/1998 | Compton | B32B 27/08 | 428/34.6 |
| 5,951,533 A * | 9/1999 | Freeman | A61F 5/443 | 604/338 |
| 6,110,197 A * | 8/2000 | Augustine | A61F 7/007 | 602/14 |
| 6,579,584 B1 * | 6/2003 | Compton | B29C 55/28 | 428/34.6 |
| 6,583,220 B1 * | 6/2003 | Lipman | C09J 153/02 | 525/54.3 |
| 6,602,232 B1 * | 8/2003 | Keyes | A61F 5/448 | 604/338 |
| 6,726,791 B1 * | 4/2004 | Øelund | B29C 43/18 | 156/199 |
| 7,422,578 B2 * | 9/2008 | Shan | A61F 5/448 | 604/332 |
| 7,544,336 B2 * | 6/2009 | Powell | A61L 2/26 | 206/363 |
| 7,981,099 B2 * | 7/2011 | Butler | A61F 5/441 | 604/327 |
| 8,328,779 B2 * | 12/2012 | Fenton | A61F 5/443 | 604/332 |
| 8,343,120 B2 * | 1/2013 | Smith | A61F 5/448 | 156/254 |
| 8,439,883 B1 * | 5/2013 | Johnsen | A61F 5/448 | 604/338 |
| 2003/0004477 A1 * | 1/2003 | Nielsen et al. | | 604/336 |
| 2005/0040060 A1 * | 2/2005 | Andersen | A61F 5/445 | 206/363 |
| 2007/0045300 A1 * | 3/2007 | Buhl | A61F 5/445 | 219/727 |
| 2008/0081789 A1 * | 4/2008 | Shuey | C07C 237/22 | 564/152 |
| 2008/0269700 A1 * | 10/2008 | O'Toole | A61F 5/4405 | 604/332 |
| 2009/0148661 A1 * | 6/2009 | Stroebech et al. | | 428/137 |
| 2009/0234312 A1 * | 9/2009 | O'Toole | A61F 5/4405 | 604/332 |
| 2010/0222255 A1 * | 9/2010 | Kirshenbaum | C07K 7/06 | 514/2.9 |
| 2012/0022477 A1 * | 1/2012 | Grum-Schwensen | A61F 5/443 | 604/332 |
| 2014/0039430 A1 * | 2/2014 | Richmann | A61F 5/443 | 604/344 |
| 2014/0163496 A1 * | 6/2014 | Grum-Schwensen | A61F 5/443 | 604/338 |

FOREIGN PATENT DOCUMENTS

| | | |
|---|---|---|
| JP | H06209961 A | 8/1994 |
| JP | 2004352732 A | 12/2004 |
| JP | 2009537263 A | 10/2009 |
| JP | 2010523276 A | 7/2010 |
| WO | 9807212 A1 | 4/1998 |
| WO | 9817212 A1 | 4/1998 |
| WO | 2007134612 A1 | 11/2007 |
| WO | 2010106039 A1 | 9/2010 |

* cited by examiner

OSTOMY SEALING MEMBER PACKAGE AND AN OSTOMY SEALING MEMBER THEREFORE

CROSS-REFERENCE TO RELATED APPLICATIONS

This is a National Stage Application of International Patent Application No. PCT/EP2012/064692, filed Jul. 26, 2012, which claims the benefit of and priority to European Patent No. 11175758.9, filed Jul. 28, 2011, the contents of which are incorporated fully by reference herein.

The present invention relates to an ostomy sealing member for providing a snugly and tight sealing around a stoma and a protective package for accommodating such ostomy sealing member.

Ostomy appliances are well known and may be provided as one-piece or two piece appliances. A body-side member or faceplate is attached to the wearer's abdomen and a bag is attached to the body-side member for receiving exudates from the ostomy. The bag and faceplate are permanently connected in a one-piece appliance and detachably connectable in a two piece appliance.

When using a one-piece appliance, the whole appliance including the faceplate adhesively securing the appliance to the skin is removed and replaced by a fresh appliance. In two-piece appliances, the faceplate is left in place and only the collection bag is replaced. The advantage of such a two-piece appliance over a conventional one-piece appliance is that a number of bags may be used successively with a single faceplate. The user of a two-piece appliance may therefore leave a faceplate adhesively attached to the skin for an extended period, without the discomfort, inconvenience, and skin irritation that frequent removal and replacement of an adhesive faceplate may involve, and simply remove a used bad and replace it with afresh one whenever needed. Further, a two-piece device allows for seeing the stoma while attaching the pouch over the faceplate.

It is known to place a barrier ring on the skin on the faceplate or to make a filling paste between the edge of the stoma in order to form a seal between the stoma and the ostomy appliance to avoid exudates contacting the skin around the stoma. The barrier ring is made of an adhesive material which is mouldable, bendable and stretchable for use on oval or otherwise irregularly shaped stomas. The ring is provided in the shape of a disc which is usually first placed on the skin-side of the faceplate and for fitting around the stoma and mouldable to a customized convexity in the skin surface around the stoma before placing the faceplate of the ostomy appliance on the skin. The barrier sealing ring is intended to be easy to use even for users with limited dexterity. This has to a large extend been achieved with the sealing members known in the art but with the present disclosure it is realised that an ostomy sealing member with improved user-friendliness may be provided.

Improved user-friendliness is also achieved by a package accommodating an ostomy sealing member for sealing around a stoma in relation to an ostomy appliance, said ostomy sealing member comprising a mouldable adhesive material, said sealing member having an annular periphery and an opening therein for receiving a stoma, wherein the ostomy sealing member is accommodated in a tray portion having a cavity dimensioned for snugly receiving the ostomy sealing member and which is integrally formed with a lid portion for removably closing the tray and with a hinge portion between said try and said lid portions, and wherein a first release film is provided in the cavity between the tray portion and the sealing member and wherein a second release film is provided on the sealing member on the side thereof facing the lid portion of the package.

This allows for a simple and discrete protective package accommodating an ostomy sealing member, which a user can easily store and carry in his or her hand luggage. In order to protect the ostomy sealing member in the package and to facilitate easy removal from the package, a first release film is provided in the cavity between the tray portion and the sealing member. Furthermore, a second release film is provided on the sealing member on the side thereof facing the lid portion of the package to protect the adhesive ostomy sealing member from being contaminated by residuals of exudates from the ostomy or the like weakening its adhesive capabilities.

Preferably, a projection extends from the cavity configured for receipt in the opening. Furthermore, the cavity may have an outer substantially circular contour and that said projection is substantially circular corresponding to the opening of the sealing member so that said projection is provided non-concentric in the cavity. This ensures a tight and snugly fit of the package around the ostomy sealing member.

In a preferred embodiment, the package is made of a single polymeric material flexible sheet, which is vacuum-formed to the required package shape. Hereby, an inexpensive manufacturing of the package may be achieved.

In one preferred embodiment, the lid portion is provided with a peripheral outer contour for snap locking over a correspondingly shaped outer contour of the tray portion for releasably closing the package. In an alternative embodiment, the lid portion is formed with at least one snap locking closure protrusion, which cooperates with at least one corresponding closure cavity of the tray portion and so that the lid portion releasably closes the package around the sealing member by snap locking the at least one closure protrusion into the at least one closure cavity of the tray portion.

According to a second aspect of the present disclosure, there is provided an ostomy sealing member for sealing around a stoma in relation to an ostomy appliance, said sealing member comprising a hypo-allergenic, mouldable adhesive material, said sealing member having an annular periphery and an opening therein for receiving a stoma, wherein the opening is non-concentric with the periphery.

By providing such an ostomy sealing member with an off-centred stoma opening, the possibility of an easier and more flexible use of a sealing member may be achieved. The off-centred sealing ring provides for forming a customized convexity and adapting the sealing for receiving an adhesive wafer for directly or indirectly securing an ostomy pouch to a person's skin depending on whether a one piece or a two piece ostomy system is used.

This ostomy sealing member is also advantageous in relation to a recently developed type of adhesive wafer which comprises a starter hole surrounded by a plurality of cutting guidelines for enabling the person to cut the hole into a desired aperture size, wherein the cutting guidelines substantially converge with the starter hole at an upper region of the hole. Such ostomy appliance is described in WO 2010/106039.

By the term "converge" should be understood that the annular cutting guidelines come close together to each other or to the hole at one region which may, but do not necessarily unite in a common point.

On the adhesive wafer the cutting guidelines substantially converge with the starter hole at a radial corresponding to the longitudinal direction of the pouch. Hereby, the "dead" volume in the head space in the top of the pouch may be minimized.

The sealing member of the present disclosure may advantageously be used in connection with such adhesive wafer with a starter hole off-centered towards the top, since the opening is off-centred from the substantially circular periphery. Accordingly, the sealing member has a varying radial width of material around the annular periphery. This is also advantageous since the sealing member according to the present disclosure may be oriented with the most and the least material corresponding to the unevenness of the surface of the skin around the stoma.

In a preferred embodiment of the sealing member, the material is mouldable so that the user can easily form the putty-like adhesive material even for users with limited dexterity in their fingers.

In one embodiment, in its form of origin the sealing member has substantially uniform thickness. This facilitates manufacturing of the sealing members. It is however realised that it may be advantageous in a variant to provide the sealing member with tapered peripheral edges at the outer periphery of the sealing member and/or the inner periphery thereof.

In order to facilitate the handling during unpacking and application of the sealing member, it is found advantageous to provide the member with a first and a second release liner on each side of the sealing member. Moreover, the sealing member is preferably accommodated in a sealing member cover preferably as a flexible tray-like structure having a cavity matching the shape of the sealing member and wherein the sealing member is accommodated with a release liner enclosed between the sealing member and the cavity surface of the flexible tray cover.

The stoma receiving opening of the sealing member may be substantially circular. This facilitates the manufacture of the sealing member. However, it is realised that other shapes may also be suitable, such as an oval shape of the outer periphery and/or the inner periphery of the sealing member.

In the following the invention is described in more detail with reference to the accompanying drawings, in which.

Figure 1:
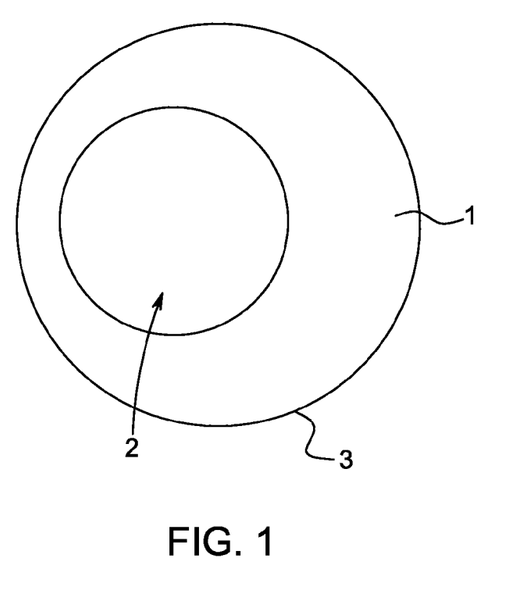
FIG. 1 is a schematic top view of an ostomy sealing member according to the invention.
Figure 2:
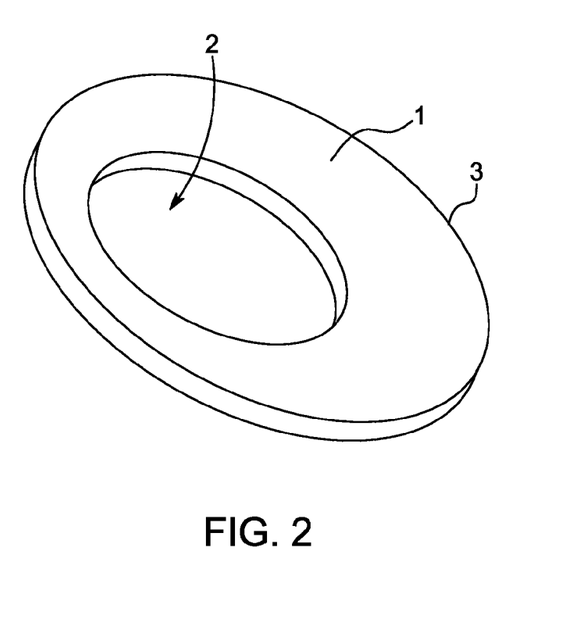
FIG. 2 is a perspective view thereof.
Figure 3:
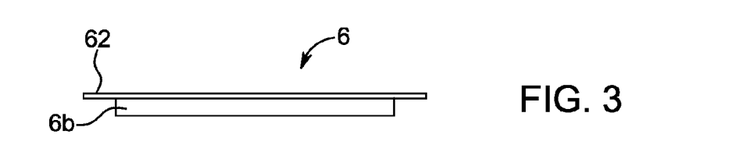
FIGS. 3 and 4 are side and top views of an ostomy sealing member package.
Figure 4:
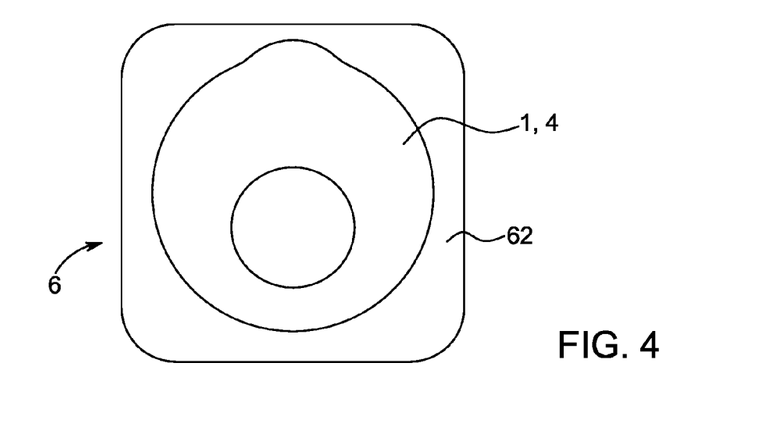
Figure 5:
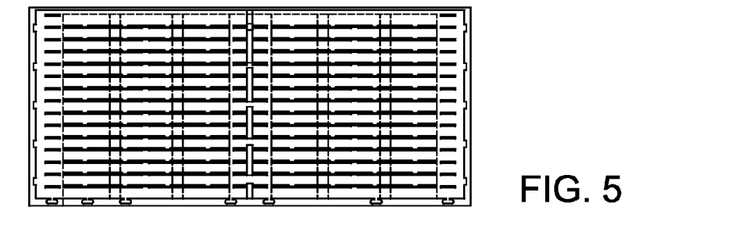
FIGS. 5 and 6 are side and top views of a multipack of ostomy sealing member packages.
Figure 6:
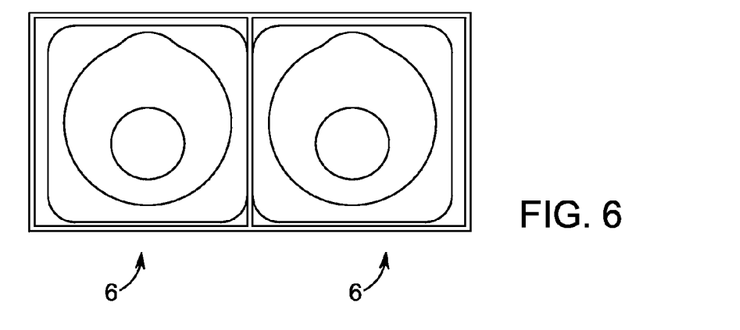
Figure 7:
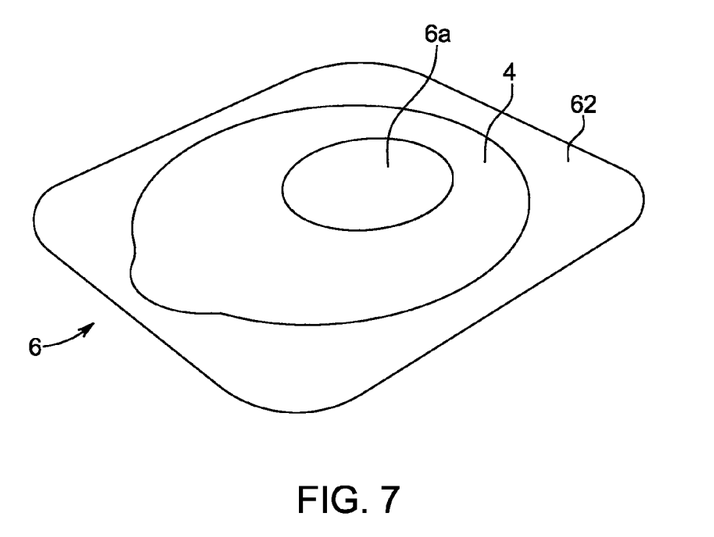
FIGS. 7 and 8 are perspective top and bottom views of a sealing member package according to a first embodiment of the invention.
Figure 8:
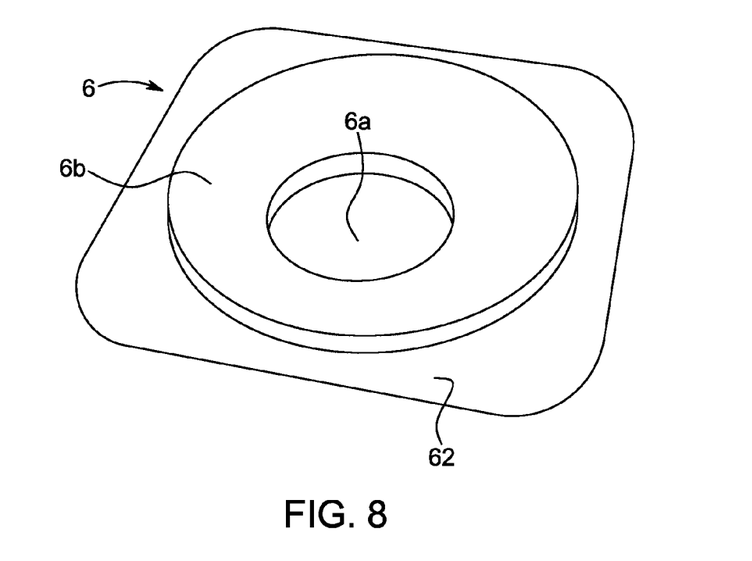
Figure 9:
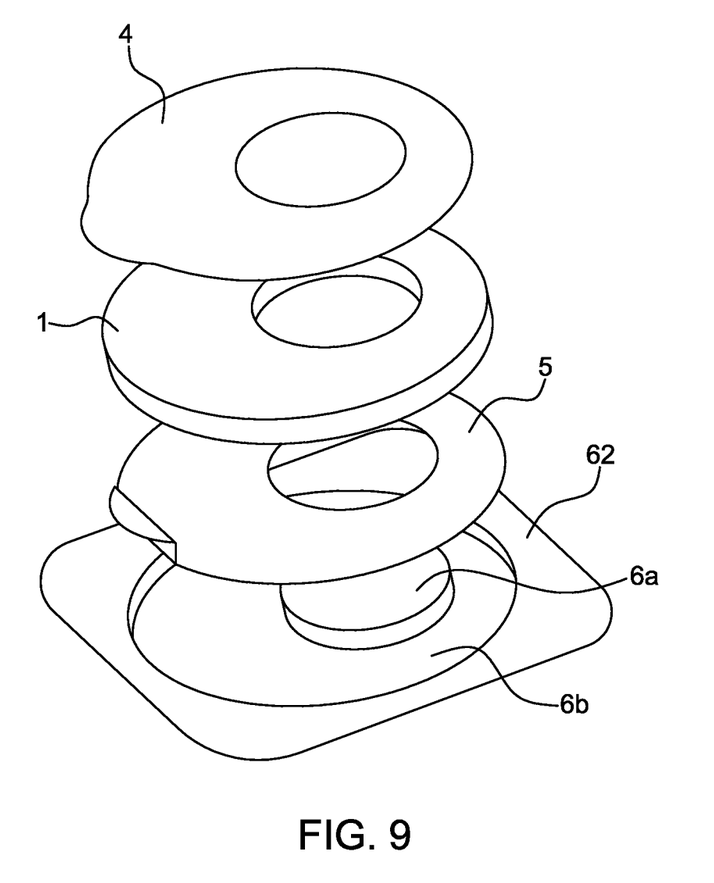
FIG. 9 is an exploded perspective view of a sealing member package according to this first embodiment of the invention.
Figure 10:
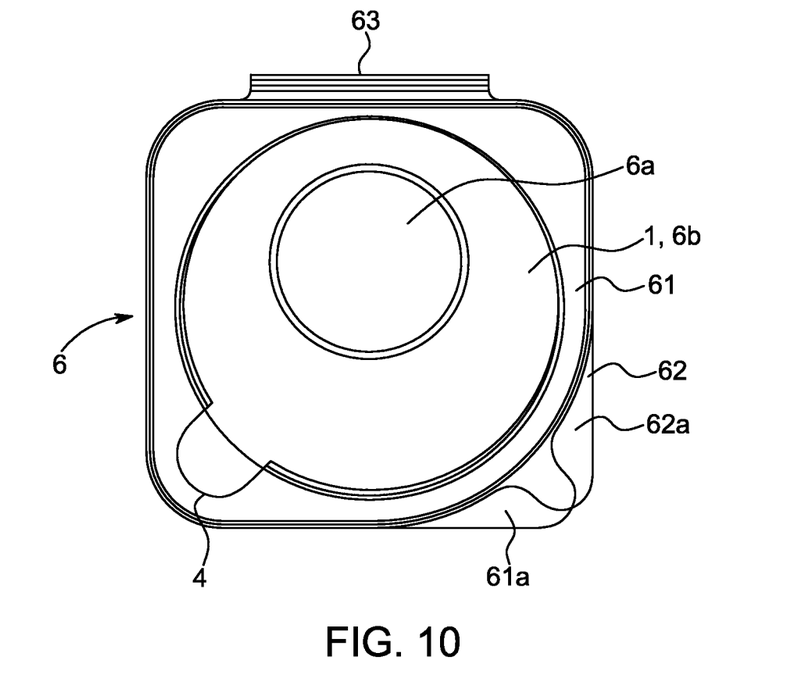
FIG. 10 is a top view of a second embodiment of a sealing member package.
Figure 11:
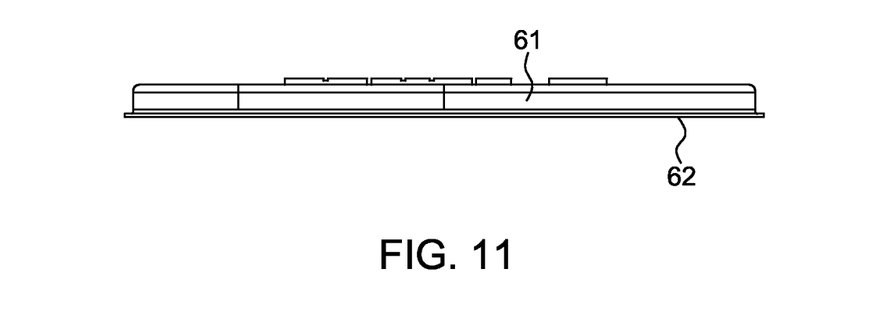
FIG. 11 is a front view of the package in FIG. 10.
Figure 12:
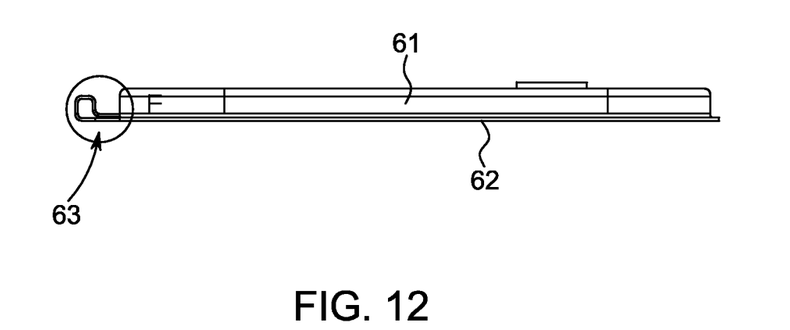
FIG. 12 is aside view of the package in FIG. 10.
Figure 13:
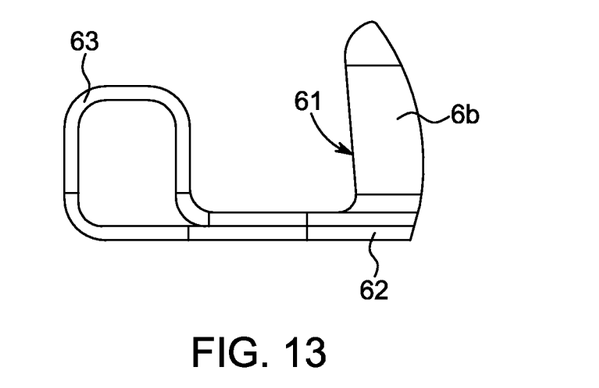
FIG. 13 is a detailed view of the hinge portion.
Figure 14:
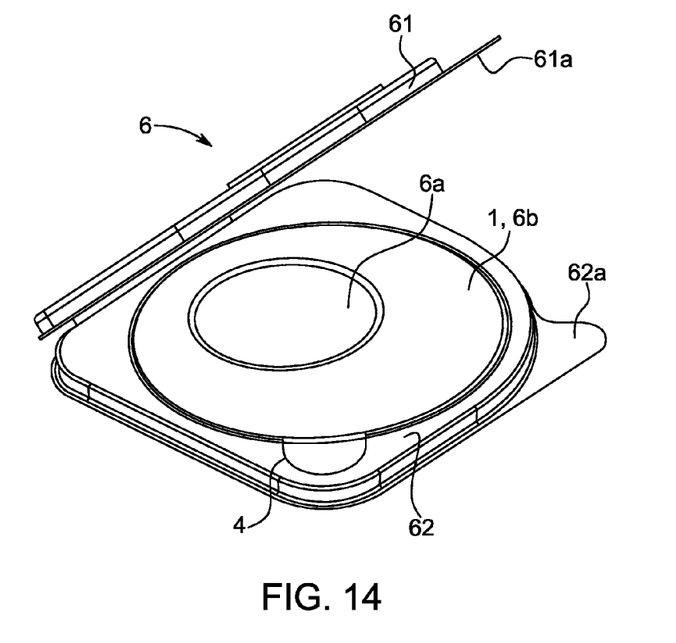
FIG. 14 is a perspective view of the sealing member package in FIG. 10 in an open position.
Figure 15:
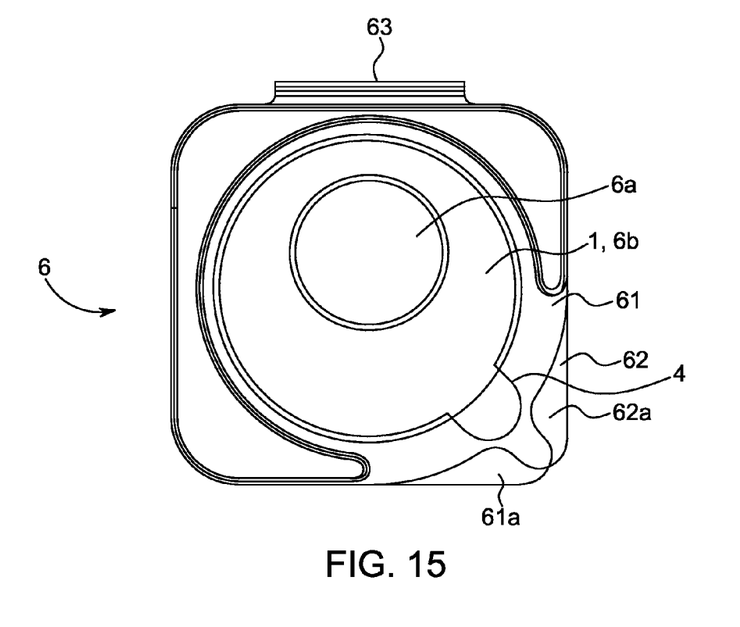
FIG. 15 is a top view of a third embodiment of a sealing member package.
Figure 16:
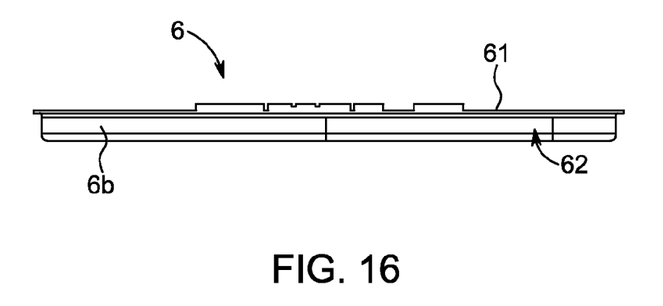
FIG. 16 is a front view of the package in FIG. 15.
Figure 17:
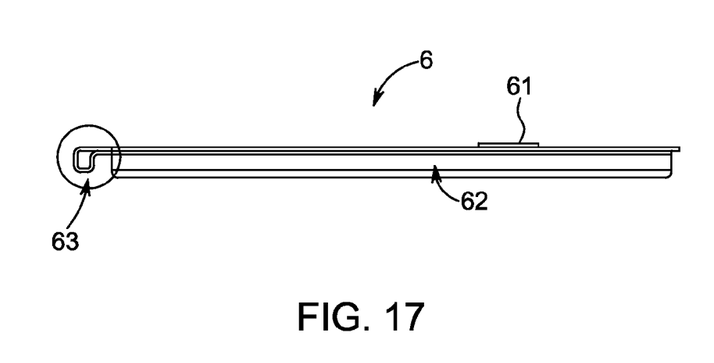
FIG. 17 is a side view of the package in FIG. 15.
Figure 18:
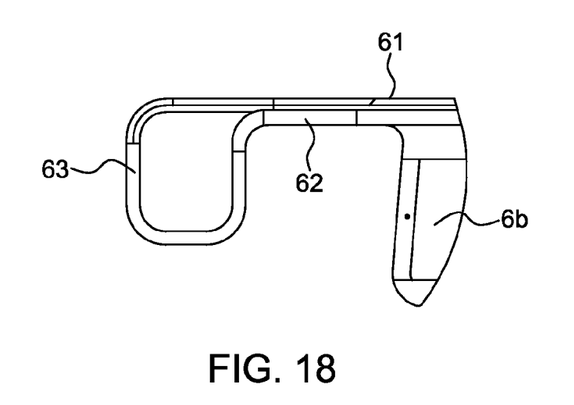
FIG. 18 is a detailed view of the hinge portion.
Figure 19:
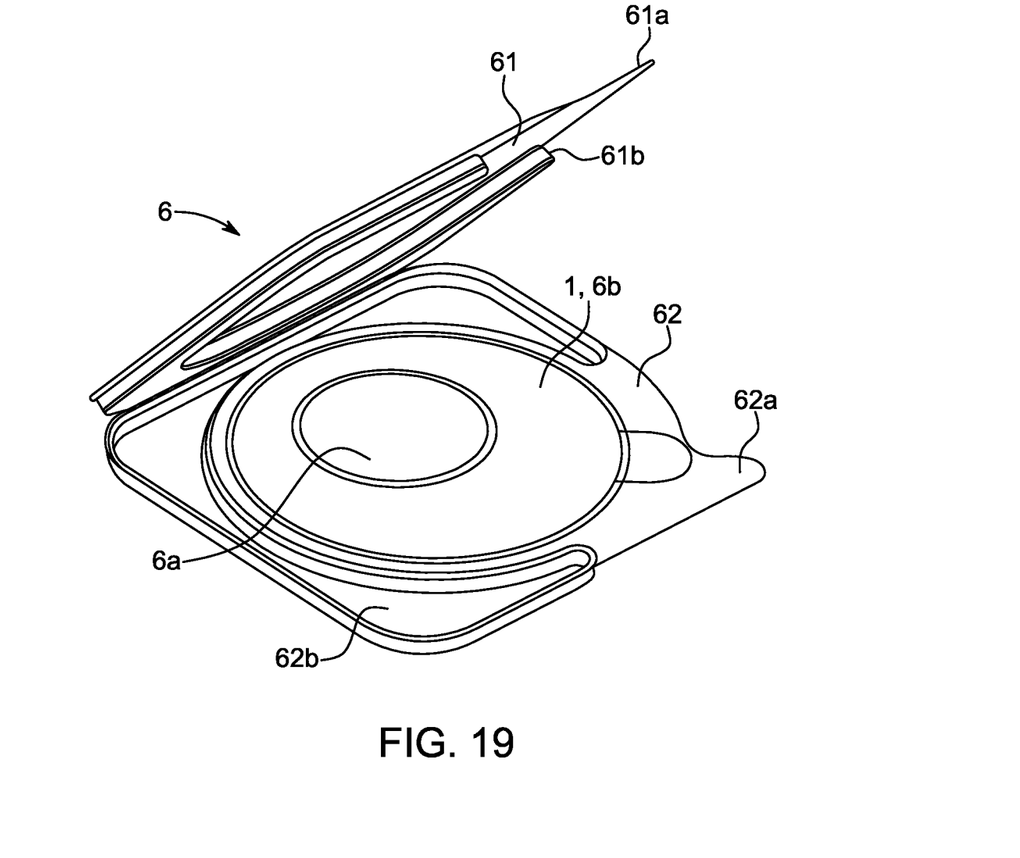
FIG. 19 is a perspective view of the sealing member package in FIG. 15 in an open position.

With reference to FIGS. 1 and 2, an ostomy sealing member for providing a snugly and tight sealing around a stoma is shown. The sealing member 1 is disc-shaped with a substantially circular outer periphery 3 and with a substantially circular stoma opening 2, which is off-centred relative to the outer periphery 3. The disc-shaped sealing member 1 is preferably provided with a substantially uniform thickness. The sealing member 1 is made of an adhesive material which is bendable, stretchable and mouldable whereby the user is able to adapt the sealing member to the actual size and form of the stoma. A presently particularly suitable material is available under the trade name "Flextend M", The sealing member 1 is preferably supplied in individual packages 6, such as shown in the various embodiments in the FIGS. 3 to 19. Due to the adhesive material of the sealing member, the sealing member 1 is provided with a first, outermost release film 4 and a second, innermost release film 5 and accommodated in a tray 62 (see e.g. FIG. 9) with an annular cavity 6b wherein the sealing member 1 is accommodated and with a protrusion 6a supporting the stoma opening 2 of the sealing member 1. The annular cavity 6b is dimensioned so that the tray 62 and thereby also the package 6 snugly fits around the sealing member 1. A first embodiment of the package 6 is shown in FIGS. 3 to 9. As shown in the figures, the cavity 6b is formed with a generally circular outer peripheral contour and an inner annular periphery formed by a protrusion 6a, which appears non-concentric relative to the outer periphery. After the sealing member 1 is fitted into the cavity 6b of the tray 62, a cover film (not shown) may be applied. As shown in FIGS. 5 and 6, the packages 6 may be stacked in for instance two stacks and wrapped or boxed together. As shown in the exploded view in FIG. 9, the ostomy sealing member 1 is provided with a top and bottom release liner 4, 5 on each side of the sealing member 1. The second release liner 5 is provided with a gripping tab extending from the outer periphery to facilitate gripping and thereby removal from the tray. The first release liner 4 is also provided with a gripping tab for easy removal so as to expose the adhesive surface of the sealing member once the sealing member has been removed from the package 6.

In FIGS. 10 to 14 and FIGS. 15 to 19, respectively, two other embodiments of a package for an ostomy sealing member are shown.

With reference to the FIGS. 10-14, the package 6 includes a tray portion 62 and a lid portion 61 which are integrally formed with a hinge portion 63 there between. The tray portion 62 is provided with the annular cavity 6b and the protrusion 6a for closely fitting the sealing member 1 in the cavity 6b. In this embodiment, the lid portion 61 is formed so that it narrowly circumscribes the outer contour of the tray portion 62 and so that the lid portion 61 releasably closes the package around the sealing member 1 by snap locking around the tray portion 62. Grip portions 61a, 62a are provided on both the lid and the tray portions 61, 62 which are shaped for easy gripping in order to open the package 6.

The lid portion 61, tray portion 62, and the hinge portion 63 are integrally formed for instance by blow moulding of a plastic film or injection moulding the package portions from a plastic material.

With reference to the FIGS. 15-19, the package 6 like the embodiment above includes a tray portion 62 and a lid portion 61 which are integrally formed with a hinge portion 63 there between. The lid portion 61, tray portion 62, and the hinge portion 63 are integrally formed for instance by vacuum-forming or blow moulding of a plastic film or injection moulding the package portions from a plastic material. The tray portion 62 is provided with the annular cavity 6b and the protrusion 6a for closely fitting the sealing member 1 in the cavity 6b.

However in this embodiment, the lid portion 61 is formed with at least one snap locking closure protrusion 61b which cooperates with corresponding closure cavity 62b of the tray portion 62 and so that the lid portion 61 releasably closes the package around the sealing member 1 by snap locking the closure protrusion 61b into the closure cavity 62b of the tray portion 62. Grip portions 61a, 62a are provided on both the lid and the tray portions 61, 62 which are shaped for easy gripping in order to open the package 6.

The invention claimed is:

1. A package accommodating an ostomy sealing member for sealing around a stoma in relation to an ostomy appliance,
   said ostomy sealing member comprising a mouldable adhesive material, said ostomy sealing member being substantially disc-shaped having an annular periphery and an opening therein for receiving a stoma,
   wherein the ostomy sealing member is accommodated in a tray portion having a cavity with a substantially circular outer contour dimensioned for snugly receiving the ostomy sealing member and which is integrally formed as one piece with a lid portion and a living hinge portion, the lid portion for removably closing the tray portion and the living hinge portion is disposed between said tray and said lid portions,
   wherein a first release film is provided in the cavity between the tray portion and the ostomy sealing member the first release film having a first aperture,
   wherein a second release film is provided on the ostomy sealing member on the side thereof facing the lid portion of the package, the second release film having a second aperture,
   wherein a projection extends from the cavity configured for receipt in the opening, and
   wherein the lid portion is provided with a peripheral outer contour for snap locking over a correspondingly shaped outer contour of the tray portion for releasably closing the package.

2. The package according to claim 1, wherein said projection is substantially circular corresponding to the opening of the ostomy sealing member so that said projection is provided non-concentric in the cavity.

3. The package according to claim 1, wherein the package is made of a single polymeric material flexible sheet, which is vacuum-formed to the required package shape.

4. The package according to claim 1, wherein the peripheral outer contour of the lid portion is formed with at least one snap locking closure protrusion, which cooperates with at least one corresponding closure cavity of the outer contour of the tray portion and so that the lid portion releasably closes the package around the ostomy sealing member by snap locking the at least one closure protrusion into the at least one closure cavity of the tray portion.

5. The package according to claim 1, wherein the ostomy sealing member is adapted for sealing around a stoma in relation to an ostomy appliance and comprises a mouldable adhesive material, wherein the opening is non-concentric with the annular periphery.

6. The package according to claim 5, wherein the opening is off-centred from an outer substantially circular contour of the cavity.

7. The package according to claim 5, wherein the ostomy sealing member has a substantially uniform thickness.

8. The package according to claim 5, wherein said ostomy sealing member is accommodated in a sealing member cover.

9. The package according to claim 5, wherein the opening is substantially circular.

10. The package according to claim 1, wherein the tray portion, the lid portion and the hinge portion are integrally formed by injection molding or blow molding.

11. The package according to claim 1, wherein the tray portion includes a grip portion.

12. The package according to claim 1, wherein the lid portion includes a grip portion.

13. The package according to claim 1, wherein the lid portion includes a first peripheral recess and a first grip portion, and the tray portion includes a second peripheral recess and a second grip portion, wherein the first grip portion overlies at least a portion of the second peripheral recess, and the second grip portion underlies at least a portion of the first peripheral recess.

14. The package according to claim 1, wherein the first release film includes a first gripping tab extending from an outer periphery of the first release film.

15. The package according to claim 14, wherein the second release film includes a second gripping tab extending from an outer periphery of the second release film.

* * * * *

UNITED STATES PATENT AND TRADEMARK OFFICE
CERTIFICATE OF CORRECTION

| | | |
|---|---|---|
| PATENT NO. | : 9,629,779 B2 | Page 1 of 1 |
| APPLICATION NO. | : 14/233059 | |
| DATED | : April 25, 2017 | |
| INVENTOR(S) | : Christen Grum-Schwensen et al. | |

It is certified that error appears in the above-identified patent and that said Letters Patent is hereby corrected as shown below:

On the Title Page

Item (57), Abstract, Column 2, Line 4, "moldable" to read as --mouldable--.

In the Specification

Column 1, Line 36, "bad" to read as --bag--.

Column 1, Line 36, "afresh" to read as --a fresh--.

Column 3, Line 59, "aside" to read as --a side--.

Column 4, Line 15, ""Flextend M"," to read as --"Flextend M".--.

In the Claims

Column 5, Lines 34-35, Claim 1, "member the" to read as --member, the--.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*